United States Patent [19]

Nakai et al.

[11] Patent Number: 4,481,362

[45] Date of Patent: Nov. 6, 1984

[54] PROCESS FOR PREPARING OPTICALLY ACTIVE TRYPTOPHANES

[75] Inventors: Mamoru Nakai; Tokio Ohshima; Tomio Kimura; Tetsuo Omata; Noritada Iwamoto, all of Yamaguchi, Japan

[73] Assignee: Ube Industries, Inc., Yamaguchi, Japan

[21] Appl. No.: 494,692

[22] Filed: May 17, 1983

Related U.S. Application Data

[63] Continuation of Ser. No. 276,057, Jun. 22, 1981, abandoned.

[30] Foreign Application Priority Data

Jun. 24, 1980 [JP] Japan .................................. 55-84618

[51] Int. Cl.³ ............................................ C07D 209/20
[52] U.S. Cl. ................................... 548/498; 548/497; 435/280
[58] Field of Search ....................... 548/498; 435/280

[56] References Cited

FOREIGN PATENT DOCUMENTS 10146  3/1958  Japan .................................. 548/497
15541  8/1967  Japan .................................. 548/497
268326  5/1950  Switzerland ........................ 548/499

OTHER PUBLICATIONS

Chibata et al., Bull. Agr. Chem. Soc. Japan, vol. 21, No. 1, pp. 62-66, (1951).
Merck Index 9th Ed., Entry 8815, Merck & Co., Rahway, N.J., (1976).

Primary Examiner—Richard Raymond
Assistant Examiner—D. B. Springer
Attorney, Agent, or Firm—Austin R. Miller

[57] ABSTRACT

Biochemical optical resolution of DL-tryptophanes in which DL-tryptophane amides are interacted with the culture products, or their treated products, of a microorganism capable of producing amidase is described. L-tryptophane amides in racemic DL-tryptophane amides are asymmetrically hydrolyzed to form optically active L-tryptophanes at a high yield and almost all D-tryptophane amides remain without being subjected to hydrolysis. The resultant D-tryptophane amides are readily hydrolyzed, after separating L-tryptophanes, to form optically active D-tryptophanes at a high yield.

9 Claims, No Drawings

PROCESS FOR PREPARING OPTICALLY ACTIVE TRYPTOPHANES

This application is a continuation of Ser. No. 276,057, June 22, 1981, abandoned.

BACKGROUND OF THE INVENTION

1. Field of the Invention

The present invention relates to a process for preparing optical active tryptophanes by biochemical asymmetric hydrolysis of DL-tryptophane amides, in which an amidase derived from a microorganism is utilized.

2. Description of the Prior Art

It is well-known in the art that L-tryptophanes and D-tryptophanes are optically active and have different properties and uses. For instance, L-tryptophane is an important compound as an essential amino acid and is suitable for use in an amino acid infusion solution, animal food stuff additives, hypnotizing agent and the like. On the other hand, D-tryptophane is useful as, for example, dentifrice additives.

Many organic synthesis methods for preparing tryptophanes have been heretofore proposed. However, when the tryptophanes are prepared by organic synthesis methods, the products are obtained in the form of mixtures of D-tryptophanes and L-tryptophanes, i.e. racemic mixtures. Therefore, the effective optical resolution of DL-tryptophanes is an extremely important problem to be solved in the art.

Proposed optical resolution methods of DL-tryptophanes are only those in which hydantoin or N-acyl derivatives of DL-tryptophanes are used as a substrate and in which microorganisms capable of producing hydantoinase or acylase are interacted with the substrate. Thus, the development of the substrate and the microorganisms used in the field of the biochemical optical resolution of DL-tryptophanes are extremely limited.

SUMMARY OF THE INVENTION

Accordingly, an object of the present invention is to obviate the afore-mentioned problems in the prior arts and to provide a novel biochemical optical resolution of DL-tryptophanes in which L-tryptophanes and D-tryptophanes can be separated from each other at a high yield.

Another object of the present invention is to selectively hydrolyze L-tryptophane amides, whereby optical active L-tryptophanes are prepared at a high yield. L-tryptophanes are prepared at a high yield.

A further object of the present invention is to hydrolyze D-tryptophane amides after the separation of L-tryptophanes from DL-tryptophane amides, whereby optical active D-tryptophanes are prepared at a high yield.

Other objects and advantages of the present invention will be apparent from the description set forth hereinbelow.

In accordance with the present invention, there is provided a process for preparing optically active L-tryptophanes having a general formula

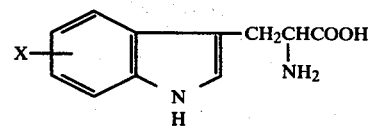

wherein X represents hydrogen, hydroxyl group, halogen atoms such as fluorine, chlorine, bromine and iodine, lower alkyl groups, preferably having 1 to 4 carbon atoms, or lower alkoxy groups, preferably having 1 to 4 carbon atoms, comprising the step of interacting DL-tryptophane amides having a general formula.

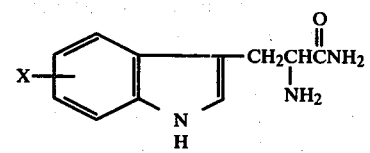

wherein X is as defined above with the culture product of a microorganism capable of producing amidase or the treated product thereof, whereby the asymmetric hydrolysis of L-tryptophane amides is effected.

In accordance with the present invention, there is also provided a process for preparing optically active D-tryptophanes having a general formula

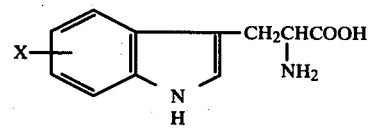

wherein X is as defined above, comprising the steps of:

(a) interacting DL-tryptophane amides having a general formula,

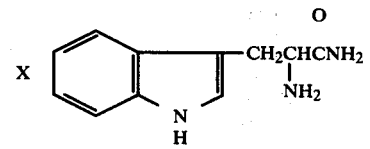

wherein X is as defined above with the culture product of a microorganism capable of producing amidase or the treated product thereof, whereby the asymmetric hydrolysis of L-tryptophane amides is effected;

(b) separating the resultant L-tryptophanes obtained from the asymmetric hydrolysis of L-tryptophane amides, and;

(c) hydrolyzing the resultant D-tryptophane amides.

DETAILED DESCRIPTION OF THE INVENTION

Biochemical asymmetric hydrolysis of DL-tryptophane amides in which an enzyme derived from animal visceral organs is employed is reported [see: Bull. Agr. Chem. Soc. Japan, Vol. 21, No. 1, P. 62–66 (1957)]. However, the biochemical asymmetric hydrolysis of DL-tryptophane amides in which there is employed an enzyme derived from microorganisms has not been reported.

According to the present invention, new substrates are provided in the biochemical optical resolution of DL-tryptophanes in which an enzyme derived from microorganisms is employed and the variety of the microorganisms which can be utilized in the optical resolution is widened. Thus, the present invention is industrially very valuable in this field.

The DL-tryptophane amides employed as a substrate in the practice of the present invention can be readily synthesized by, for example, reacting the esters of DL-tryptophanes with ammonia in a conventional manner.

The microorganisms which can produce the amidase used in the practice of the present invention are those which belong to any systematic group, so long as they have the capability of selectively hydrolyzing only L-tryptophane amides in the racemic mixtures of DL-tryptophane amides. Examples of the genus names of these microorganisms are listed in the following Table, in which the typical species name of the microorganism belonging to each genus is also listed. However, it should be noted that the microorganisms which can be employed in the practice of the present invention are not limited to these specific examples. All the exemplified microorganisms are known and also readily available from the depositories of JFCC (Japanese Federation of Culture Cellections of Microorganisms) such as IFO (Institute for Fermentation, Osaka, Japan) and IAM (Institute of Applied Microbiology, University of Tokyo, Tokyo, Japan).

TABLE

| NAME OF MICROORGANISMS | DEPOSIT NO. |
|---|---|
| (1) Genus Rhizopus<br>*Rhizopus Chinensis* | IFO-4768 |
| (2) Genus Absidia<br>*Absidia Orchidis* | IFO-4011 |
| (3) Genus Penicillium<br>*Penicillium frequentans* | IFO-5692 |
| (4) Genus Pullularia<br>*Pullularia pullulans* | IFO-4464 |
| (5) Genus Fusarium<br>*Fusarium roseum* | IFO-5421 |
| (6) Genus Gibberella<br>*Gibberella fujikuroi* | IFO-5268 |
| (7) Genus Trichoderma<br>*Trichoderma viride* | IFO-4847 |
| (8) Genus Gliocladium<br>*Gliocladium roseum* | IFO-5422 |
| (9) Genus Cunninghamella<br>*Cunninghamella elegans* | IFO-4441 |
| (10) Genus Actinomucor<br>*Actinomucor repens* | IFO-4022 |
| (11) Genus Geotrichum<br>*Geotrichum candidum* | IFO-6454 |
| (12) Genus Saccharomyces<br>*Saccharomyces rouxii* | IFO-0505 |
| (13) Genus Shizosaccharomyces<br>*Shizosaccharomyces pombe* | IFO-0346 |
| (14) Genus Pichia<br>*Pichia polimorpha* | IFO-0195 |
| (15) Genus Hansenula<br>*Hansenula anomala* | IFO-0117 |
| (16) Genus Debariomyces<br>*Debariomyces hansenii* | IFO-0023 |
| (17) Genus Nadsonia<br>*Nadsonia elongata* | IFO-0665 |
| (18) Genus Sporobolomyces<br>*Sporobolomyces pararoseus* | IFO-0376 |
| (19) Genus Cryptococcus<br>*Cryptococcus albidus* | IFO-0378 |
| (20) Genus Torulopsis<br>*Torulopsis candida* | IFO-0768 |
| (21) Genus Brettanomyces<br>*Brettanomyces anomalus* | IFO-0642 |
| (22) Genus Candida<br>*Candida utilis* | IFO-0396 |
| (23) Genus Tricosporon<br>*Tricosporon beigelii* | IFO-0598 |
| (24) Genus Rhodotorula<br>*Rhodotorula minuta* var *texensis* | IFO-0412 |
| (25) Genus Mycobacterium<br>*Mycobacterium phlei* | IFO-3158 |
| (26) Genus Nocardia<br>*Nocardia asteroides* | IFO-3424 |
| (27) Genus Streptomyces<br>*Streptomyces griseus* | IFO-3356 |
| (28) Genus Enterobacter<br>*Enterobacter aerogenes* | IFO-3320 |
| (29) Genus Alcaligenes<br>*Alcaligenes viscolactis* | IAM-1517 |
| (30) Genus Flavobacterium<br>*Flavobacterium arborescens* | IAM-1100 |
| (31) Genus Bacillus<br>*Bacillus subtilis* | IFO-3026 |
| (32) Genus Agrobacterium<br>*Agrobacterium tumefaciens* | IFO-13262 |
| (33) Genus Micrococcus<br>*Micrococcus flavus* | IFO-3242 |
| (34) Genus Sarcina<br>*Sarcina aurantiaca* | IFO-3064 |
| (35) Genus Arthrobacter<br>*Arthrobacter simplex* | IFO-3530 |
| (36) Genus Brevibacterium<br>*Brevibacterium ammoniagenes* | IFO-12071 |
| (37) Genus Pseudomonas<br>*Pseudomonas fluorescens* | IFO-3081 |
| (38) Genus Lactobacillus<br>*Lactobacillus casei* | IFO-3322 |
| (39) Genus Streptococcus<br>*Streptococcus lactis* | IFO-3434 |
| (40) Genus Clostridium<br>*Clostridium acetobutyricum* | IFO-3346 |
| (41) Genus Klebsiella<br>*Klebsiella Pneumonia*<br>(as *Aerobacter aerogenes*) | IFO-3317 |
| (42) Genus Achromobacter<br>*Achromobacter cycloclastes* | IAM-1013 |

Among these microorganisms, microorganisms belonging to genera Trichoderma, Rhodotorula, Nocardia, Mycobacterium, Bacillus, Rhizopus, Candida, Hansenula, Streptomyces, Aerobacter, Arthrobacter, Pseudomonas, Gibberella, Torulopsis and Enterobacter are especially useful in the practice of the present invention.

In the practice of the present invention, the above mentioned microorganisms can be interacted with the DL-tryptophane amides in the form of either the culture products obtained from the cultivation of cells in liquid culture media or the treated products thereof. Examples of the treated products are the cells isolated from the culture solutions, the enzyme (i.e. amidase) isolated from the culture products or the strains according to any conventional enzyme isolating technique (e.g. the crude enzyme, the purified enzyme, the enzyme-containing extracts or the concentrated solutions thereof). The cells or enzymes can be immobilized on carriers in the practice of the present invention.

Examples of the carriers are natural products such as alginic acid, carrageenan, collagen, cellulose, acetylcellulose, agar-agar, cellophane, collodion and the like, and synthetic polymer substances such as polyacrylamide, polystyrene, polyethylene glycol, polypropylene glycol, polyurethane, polybutadiene and the like. The immobilization of the cells or enzymes on the carrier can be carried out in a conventional manner under moderate conditions so that the activity of amidase is not impaired.

The suitable reaction temperature of the asymmetric hydrolysis according to the present invention can be within the range of from 20° to 50° C. However, in order to minimize the decrease in the enzymatic activity, the use of the reaction temperature of from 25° to 40° C. is economically advantageous.

The suitable reaction time of the asymmetric hydrolysis according to the present invention can be within the range of from 5 to 50 hours. However, the reaction time can be shortened by raising the reaction temperature or by increasing the amount of the enzymes used. Furthermore, the reaction can be generally carried out under a pH of 5 through 10, more preferably 7 through 9.

The amount of the microorganisms employed in the practice of the present invention is preferably in a weight ratio of from 0.01 to 2, in terms of the freeze dried cells, based on the weight of the DL-tryptophane amides. In the case where the cultivation mixtures of the microorganisms, treated products thereof, or the immobilized products thereof are employed, the amount thereof can be determined in terms of the amount of the freeze dried cells. The suitable concentration of the substrate, i.e. DL-tryptophane amides in the reaction mixture is generally within the range of from 1 to 40% by weight, more preferably 5 to 30% by weight.

According to the present invention, the asymmetric hydrolysis reaction is stopped after the hydrolysis of L-tryptophane amide proceeds at the conversion rate of almost 100%, and, then, L-tryptophanes and D-tryptophane amides are separately isolated from the reaction mixture. This separation can be readily carried out by using any conventional separation techniques, such as fractional crystallization and solvent extraction.

D-tryptophane amides are not affected by the action of the microorganisms in the above mentioned asymmetric hydrolysis and, therefore, almost all D-tryptophane amides can be recovered from the racemic mixture. The D-tryptophane amides thus recovered can be readily hydrolyzed by using any conventional technique, for example, by heating in the presence of an aqueous acid or alkaline solution. Thus, optically active D-tryptophane can be obtained at a high yield. The D-tryptophane amides recovered above can also be subjected to a racemization and reused as a substrate in the asymmetric hydrolysis of the present invention.

The optical purity and yield of the L-tryptophanes as well as the D-tryptophanes are equal to or more than those obtained from known biochemical optical resolution.

EXAMPLES

The present invention will now be further illustrated by, but is by no means limited to, the following Examples wherein the yield of L- or D-tryptophanes is calculated from the following equation.

$$\text{Yield (\%)} = \frac{\text{moles of the resultant L- or D-tryptophanes}}{\text{moles of the L- or D-tryptophane amides in the starting substrate}} \times 100$$

EXAMPLES 1 THROUGH 15

100 ml of a culture medium having a pH of 7.0 and containing 5% by weight of glycerol, 5% by weight of corn steep liquor, 0.5% by weight of ammonium sulfate and 1 ml of a mixture of inorganic salts was charged into a shaking flask. The inorganic salt mixture was prepared by dissolving 20 g of $MgSO_4 \cdot 7H_2O$, 5 g of $FeSO_4 \cdot 7H_2O$, 2 g of $CaCl_2$, 0.2 g of $MnCl_2 \cdot 4H_2O$, 0.1 g of $Na_2MoO_4 \cdot 2H_2O$ and 0.1 g of NaCl in 1000 ml of distilled water. After sterilizing the content of the flask, 2 loopful of each of the microorganisms listed in Table 1 below were inoculated from an agar slant and, then, the reciprocal shaking culture (or incubation) was carried out at a temperature of 30° C. for 65 hours.

Thereafter, 2 g of DL-tryptophane amide was added to the flask and, then, the reciprocal shaking culture was carried out for 48 hours at a temperature of 30° C. The cells was removed from the reaction mixture by centrifugation or filtration. The pH of the culture filtrate was adjusted to 6.0 and, then, the filtrate was vacuum concentrated until the volume of the filtrate became 5 through 10 ml. The crystallized L-tryptophane was collected by filtration after cooling.

The results are shown in the following Table 1.

TABLE 1

| | | | Formed L-Tryptophane | |
|---|---|---|---|---|
| Example No. | Microorganism as used | | Isolation Yield (%) | Optical Rotation $[\alpha]_D^{20}$ (C = 0.5, $H_2O$) |
| 1 | Enterbacter aerogenes | IFO-3317 | 52 | −31.5° |
| 2 | Bacillus Subtilis | IFO-3026 | 47 | −30.5° |
| 3 | Candida utilis | IFO-0396 | 44 | −31.2° |
| 4 | Rhodotorula glutinis var. rebescens | IFO-0413 | 54 | −33.0° |
| 5 | Rhizopus chinensis | IFO-4768 | 51 | −32.0° |
| 6 | Trichoderma Viride | IFO-4847 | 27 | −30.0° |
| 7 | Nocardia asteroides | IFO-3424 | 29 | −29.8° |
| 8 | Mycobacterium phlei | IFO-3158 | 25 | −31.0° |
| 9 | Streptomyces griseus | IFO-3356 | 30 | −29.5° |
| 10 | Klebsiella pneumoniae (as Aerobacter aerogenes) | IFO-3320 | 32 | −30.0° |
| 11 | Arthrobacter simplex | IFO-3530 | 37 | −31.8° |
| 12 | Pseudomonas fluorescens | IFO-3081 | 28 | −32.0° |
| 13 | Gibberella fujikuroi | IFO-5268 | 31 | −29.5° |
| 14 | Torulopsis candida | IFO-0768 | 23 | −29.8° |
| 15 | Hansenula anomala | IFO-0117 | 26 | −30.5° |

EXAMPLE 16

From the culture solution of Rhodotorula glutinis var. rebescens prepared in a manner as described in Example 4, the cells was collected by centrifugation and, then, washed twice with distilled water.

The washed cells were added to 100 ml of a 0.1M phosphate buffer solution having a pH of 7.0 and containing 2 g of DL-tryptophane amide and the mixture was incubated for 20 hours at a temperature of 30° C.

After the completion of the reaction, the cells were removed from the reaction mixture by centrifugation. The reaction mixture thus obtained was analyzed by high speed liquid chromatography. The resultant reaction mixture contained 983 mg of L-tryptophane (yield: 98%) and 1010 mg of D-tryptophane amide. From this reaction mixture the unreacted D-tryptophane amide was extracted by using ethyl acetate.

On the other hand, the pH of the water layer after the extraction was adjusted to 5.9 by using 2N sulfuric acid. Then, the resultant solution was vacuum concentrated until the total volume of the solution became about 20 ml. After ice-cooling, 330 mg of the crystallized L-tryptophane having a melting point of 280°–282° C. (decomposition) and $[\alpha]_D^{20}$ of −33.5° (C=0.5 $H_2O$) was collected).

EXAMPLE 17

The washed cells of Rhodotolua glutinis var. rebescens prepared in a manner as described in Example 16 were washed with cold acetone. Thus, acetone dried cells were obtained.

On the other hand, DL-tryptophan amide was dissolved in distilled water and substrate solutions having various concentrations listed in Table 2 below and having a pH of 7.0 were prepared.

The above mentioned acetone dried cells were added to 10 ml of the substrate solution in such an amount that a weight ratio of the dried cells to the substrate were 0.2. Then, the reaction was carried out at a temperature of 30° C. for 20 hours. The resultant reaction mixture was analyzed to determine the yield of L-tryptophane by using high speed liquid chromatography.

The results are shown in Table 2 below.

TABLE 2

| Concentration of Substrate (i.e. DL-Tryptophane Amide) | Yield (%) of L-Tryptophane |
| --- | --- |
| 1 | 100 |
| 2 | 100 |
| 5 | 100 |
| 10 | 100 |
| 20 | 92 |
| 30 | 75 |
| 40 | 55 |

EXAMPLE 18

The washed cells of Rhodotorula glutinis var. rebescens prepared in a manner as described in Example 16 were freeze dried.

The freeze dried cells were added to 10 ml of distilled water containing 10% by weight of DL-tryptophane amide (pH=7.5) in the weight ratio of the cells to the substrate listed in Table 3 below. Then, mixture was incubated at a temperature of 30° C. for 20 hours.

The reaction mixture was analyzed to determine the yield of L-tryptophane by high speed liquid chromatography.

The results are shown in Table 3 below.

TABLE 3

| Freeze Dried Cells/Substrate (weight ratio) | Yield (%) of L-tryptophane |
| --- | --- |
| 0.01 | 73 |
| 0.05 | 98 |
| 0.1 | 100 |
| 0.5 | 100 |
| 1.0 | 100 |

EXAMPLE 19

50 mg of the freeze dried cells of Rhodotorula glutinis var. rebescens prepared in a manner as described in Example 18 were suspended in 5 ml of 0.2M phosphate acid buffer solution and, then, the cells were disrupted under cooling by using a French press (20,000 psi). The resultant mixture was centrifuged under 20,000×g for 30 mins. To 5 ml of the supernatant solution thus obtained, 250 mg of DL-tryptophane amides was added and the pH of the mixture was adjusted to 7.5. Thereafter, the mixture was incubated at a temperature of 30° C. for 20 hours.

The reaction mixture was analyzed by a high speed liquid chromatography. L-tryptophane was obtained at a yield of 95%.

EXAMPLE 20

To 5 ml of the cell-free extract of Rhodotorula glutinis var. rebescens prepared in a manner as described in Example 19, ammonium sulfate was added. The protein which was precipitated at a saturation of 25 to 75% was collected by centrifugation. Then, 5 ml of 0.2M phosphate buffer solution containing 250 mg of DL-tryptophane amide and having a pH of 7.5 was added thereto and the mixture was incubated at a temperature of 30° C. for 20 hours.

The reaction mixture was analyzed by high speed liquid chromatography. L-tryptophane was obtained at a yield of 63%.

EXAMPLE 21

10 ml of the cell-free extract of Rhodotorula glutinis var. rebescens prepared in a manner as described in Example 19 was passed through a column having a diameter of 1.5 cm and a length of 65 cm and packed with Sephadex G-75 and fractions having amidase activity were collected. These fractions were concentrated by using a semipermeable membrane method to a volume of 5 ml. Then, 250 mg of DL-tryptophane amide was added thereto and the mixture was incubated at a temperature of 30° C. for 20 hours.

The reaction mixture was analyzed by high speed liquid chromatography. L-tryptophane was obtained at a yield of 56%.

EXAMPLE 22

The washed cells (corresponding to 1.0 g of the freeze dried cells) of Rhodotorula glutinis var. rebescens prepared in a manner as described in Example 16 were suspended in 15 ml of 0.1M phosphate buffer solution having a pH of 7.0 and, then, 3.75 g of acrylamide monomer, 0.2 g of N,N'-methylene bisacrylamide (i.e. crosslinking agent), 2.5 ml of a 5% aqueous 3-dimethylamino propionitrile solution (i.e. polymerization promotor) and 2.5 ml of 2.5% aqueous potassium persulfate solution (i.e. polymerization initiator) were added and mixed with one another. The mixture was allowed to stand at a temperature of 25° C. for 1 hour, whereby the gellation of the mixture was complete.

The gel thus obtained was crushed and washed with water. The resultant immobilized product, (i.e., gel particles, having a particle diameter of 0.2 to 0.5 mm) was packed into a column having a diameter of 2 cm and a length of 50 cm. Thereafter, distilled water containing 10% by weight of DL-tryptophane amide and having a pH of 7.5 was passed through the column at a temperature of 30° C. from the top of the column at a space velocity (SV) of 0.2.

In this continuous reaction, the yield of L-tryptophane was maintained at a yield of 80% or more until the reaction time became 200 hours.

EXAMPLE 23

Example 4 was repeated except that 2.0 g of DL-5-hydroxytryptophane amide was used as a substrate. As a result, L-5-hydroxytryptophane was obtained at a yield of 43%.

EXAMPLE 24

Example 15 was repeated except that 2.0 g of DL-6-methoxytryptophane amide was used as a substrate. As a result, L-6-methoxytryptophane was obtained at a yield of 27%.

EXAMPLE 25

Example 1 was repeated except that Candida kurusei (IFO-0013) was used as a microorganism and DL-5-methyltryptophane amide was used as a substrate. As a result, L-5-methyltryptophane was obtained at a yield of 23%.

EXAMPLE 26

Example 4 was repeated except that 2.0 g of DL-6-chlorotryptophane amide was used as a substrate. As a result, L-6-chlorotryptophane was obtained at a yield of 34%.

EXAMPLE 27

To 500 mg of D-tryptophane amide recovered in the manner as described in Example 16, 5 ml of concentrated hydrochloric acid was added and, then, the mixture was heated at a temperature of 90° C. for 3 hours, whereby the hydrolysis reaction was effected. After the completion of the reaction, concentrated hydrochloric acid was vacuum distilled off. 5 ml of water was added to the residue and the pH thereof was adjusted to 6.0. After ice cooling, 460 mg of the precipitated D-tryptophane having $[\alpha]_D^{20}$ of +33.3° (C=0.5 H$_2$O) was collected by filtration. The yield of the isolated D-tryptophane was 92%.

We claim:

1. A process for preparing optically active L-tryptophanes having the formula,

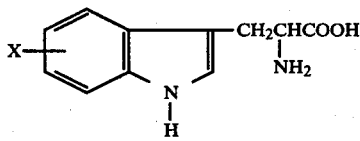

wherein X represents hydrogen, hydroxyl group, halogen atoms, lower alkyl groups or lower alkoxy groups comprising the steps of interacting a DL-tryptophane amide having the formula

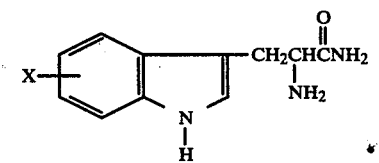

wherein X is as defined above with the culture product of a microorganism selected from the group consisting of *Rhizopus chinensis, Gibberella fujikuroi, Trichoderma viride, Torulopsis candida, Candida utilis, Mycobacterium phlei, Nocardia asteroides, Streptomyces griseus, Enterobacter cloacae, Bacillus subtilis, Pseudomonas fluorescens, Klebseiella pneumoniae,* as *Aerobacter aerogenes* and *Rhodotorula glutinis* va. rubescenes and separating the resulting L-tryptophanes from the hydrolyzed mixture.

2. A process as claimed in claim 1, wherein the reaction temperature of the asymmetric hydrolysis of L-tryptophane amides is within the range of from 20° to 50° C.

3. A process as claimed in claim 1, wherein the reaction time of the asymmetric hydrolysis of L-tryptophane amides is within the range of from 5 to 50 hours.

4. A process as claimed in claim 1, wherein the amount of the microorganism is in a weight ratio of from 0.01 to 2, in terms of the freeze dried cells, based on the weight of the DL-tryptophane amides.

5. A process for preparing optically active D-tryptophanes having the formula,

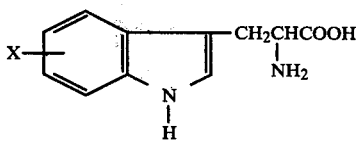

wherein X represents hydrogen, hydroxyl group, halogen atoms, lower alkyl groups or lower alkoxy groups comprising the steps of:

(a) interacting a DL-tryptophane amide having the formula

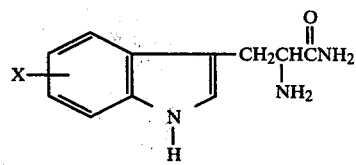

wherein X is as defined above with the culture product of a microorganism selected from the group consisting of *Rhizopus chinensis, Gibberella fujikuroi, Trichoderma viride, Torulopsis candida, Candida utilis, Mycobacterium phlei, Nocardia asteroides, Streptomyces griseus, Enterobacter cloacae, Bacillus subtilis, Pseudomonas fluroescens, Klebseiella pneumonae,* as as *Aerobacter aerogenes* and *Rhodotorula glutinis* va. rubescens whereby the asymmetric hydrolysis of L-tryptophane amides is effected;

(b) separating the resultant L-tryptophanes obtained from the asymmetric hydrolysis of L-tryptophane amides, and;

(c) hydrolyzing the resultant D-tryptophane amides.

6. A process as claimed in claim 5, wherein the reaction temperature of the asymmetric hydrolysis of L-tryptophane amides is within the range of from 20° to 50° C.

7. A process as claimed in claim 5, wherein the reaction time of the asymmetric hydrolysis of L-tryptophane amides is within the range of from 5 to 50 hours.

8. A process as claimed in claim 5, wherein the amount of the microorganism is in a weight ratio of from 0.01 to 2, in terms of the freeze dried cells based, on the weight of the DL-tryptophane amides.

9. A process as claimed in claim 5, wherein the hydrolysis of the D-tryptophane amides is carried out in the presence of an aqueous acid or alkaline solution.

* * * * *